United States Patent
O'Sullivan et al.

(10) Patent No.: US 11,771,851 B2
(45) Date of Patent: Oct. 3, 2023

(54) TESTING METHOD FOR A DRY POWDER INHALER

(71) Applicant: NORTON (WATERFORD) LIMITED, Waterford (IE)

(72) Inventors: Denis Henry O'Sullivan, Kilkeny (IE); Daniel R Buck, Waterford (IE)

(73) Assignee: NORTON (WATERFORD) LIMITED, Waterford (IE)

(*) Notice: Subject to any disclaimer, the term of this patent is extended or adjusted under 35 U.S.C. 154(b) by 0 days.

(21) Appl. No.: 17/337,325

(22) Filed: Jun. 2, 2021

(65) Prior Publication Data

US 2021/0283348 A1 Sep. 16, 2021

Related U.S. Application Data

(63) Continuation of application No. 16/477,380, filed as application No. PCT/EP2018/051023 on Jan. 16, 2018.

(30) Foreign Application Priority Data

Jan. 16, 2017 (GB) .................................. 1700727

(51) Int. Cl.
*A61M 15/00* (2006.01)
*A61M 16/14* (2006.01)
(Continued)

(52) U.S. Cl.
CPC .... *A61M 15/0008* (2014.02); *A61M 15/0001* (2014.02); *A61M 15/0086* (2013.01);
(Continued)

(58) Field of Classification Search
CPC .............. A61M 15/00; A61M 15/0001; A61M 15/0008; A61M 15/0086; A61M 15/0091;
(Continued)

(56) References Cited

U.S. PATENT DOCUMENTS 6,785,400 B1 * 8/2004 Farina .................... G01N 21/47
356/414
2003/0098968 A1 5/2003 Yang et al.
(Continued)

FOREIGN PATENT DOCUMENTS

WO 2005025536 A2 3/2005
WO 2009/029027 A1 2/2009
(Continued)

OTHER PUBLICATIONS

Murphy, "Evaluation of Plume Geometry & Spray Pattern from a Dry Powder Device using FDA Guidance", DDL24—drug delivery to the lungs UK—Dec. 11-13, 2013, Poster No. 21, 4 pages.
(Continued)

*Primary Examiner* — Harshad R Patel
*Assistant Examiner* — Gedeon M Kidanu
(74) *Attorney, Agent, or Firm* — Morgan, Lewis & Bockius LLP

(57) ABSTRACT

The invention provides a method of testing an inhaler based on performing an optical analysis of a dry powder medicament plume discharged from the inhaler upon actuation. More particularly, embodiments of the invention comprise illuminating the dry powder plume with a source of electromagnetic radiation and capturing one or more images of a pattern of radiation reflected or diffracted by the illuminated plume. The images are subsequently processed to determine and/or analyse one or more geometric and/or dynamic characteristics of the plume.

19 Claims, 10 Drawing Sheets

(51) Int. Cl.
*G01N 15/06* (2006.01)
*G01N 15/00* (2006.01)

(52) U.S. Cl.
CPC ........ *A61M 15/0091* (2013.01); *A61M 16/14* (2013.01); *G01N 15/06* (2013.01); *A61M 2202/064* (2013.01); *G01N 2015/0046* (2013.01); *G01N 2015/0693* (2013.01)

(58) Field of Classification Search
CPC ............ A61M 16/14; A61M 2202/064; G01N 15/06; G01N 2015/0046; G01N 2015/069
See application file for complete search history.

(56) References Cited

U.S. PATENT DOCUMENTS

| 2004/0069303 | A1 | 4/2004 | Brown et al. | |
|---|---|---|---|---|
| 2010/0000529 | A1 | 1/2010 | Prime et al. | |
| 2010/0238457 | A1* | 9/2010 | Adamo ................. | A61M 15/00 356/244 |
| 2011/0108030 | A1* | 5/2011 | Blair .................... | A61K 31/137 128/203.15 |
| 2012/0145150 | A1 | 6/2012 | Donovan et al. | |
| 2014/0002667 | A1 | 1/2014 | Cheben et al. | |
| 2014/0083424 | A1 | 3/2014 | Hoekman et al. | |
| 2015/0092189 | A1 | 4/2015 | Waters | |
| 2015/0226656 | A1 | 8/2015 | Adamo | |
| 2018/0344951 | A1 | 12/2018 | Shahaf | |
| 2019/0133927 | A1* | 5/2019 | Ostrovski ............. | A61M 15/00 |

FOREIGN PATENT DOCUMENTS

| WO | 2010108046 A1 | 9/2010 |
|---|---|---|
| WO | 2011/054527 A1 | 5/2011 |
| WO | 2012/078804 A1 | 6/2012 |

OTHER PUBLICATIONS

Murphy, "Understanding the affect of DPI device and lactose type on the output from a device ", DDL24—drug delivery to the lungs UK—Dec. 11-13, 2013, Poster No. 48, 4 pages.

Murphy, "Evaluation of Dry Powder Device using High-speed Imaging Techniques", DDL24—drug delivery to the lungs UK—Dec. 11-13, 2013, Poster No. 22, 4 pages.

"Envision laser-based imaging system: Fully Characterises Nasal- and Dry Powder-Based Systems", 2020, ONdrugDelivery Publishing, pp. 26-29.

International Search Report for International Application No. PCT/EP2018/051023 dated Mar. 14, 2018, 3 pages.

Written Opinion for International Application No. PCT/EP2018/051023 dated Mar. 14, 2018, 5 pages.

International Preliminary Report on Patentability for International Patent Application No. PCT/EP2018/051023 dated Jul. 16, 2019, 7 pages.

Extended European Search Report issued in corresponding EP Application No. 22213233.4 dated Mar. 28, 2023, 11 pages.

Seamus et al., "Understanding the affect of DPI device and lactose type on the output from a device", Drug Delivery to the Lungs, vol. 24, Dec. 11, 2013, Retrieved fro the Internet: URL: https://ddl-conference.com/wp-content/uploads/2016/09/48.Murphy.pdf.

* cited by examiner

TESTING METHOD FOR A DRY POWDER INHALER

This application is a Continuation of U.S. patent application Ser. No. 16/477,380 filed Jul. 11, 2019, which is a U.S. National Stage of International Patent Application No. PCT/EP2018/051023, filed Jan. 16, 2018, which claims the benefit of priority to GB Patent Application No. 1700727.9, filed Jan. 16, 2017, the entireties of which are incorporated herein by reference.

This invention relates to a testing method for a dry powder inhaler (DPI).

Dry powder inhalers (DPIs) represent one class of inhaler used for delivering inhalable medicament formulations. Other classes of inhalers include a pressurised metered dose inhalers (pMDI) and a nebuliser.

The purpose of an inhalable formulation is to present the formulation in the form of an aerosol of particles having a particle size suitable for lung deposition, which is typically a mass median aerodynamic diameter (MMAD) of 1-5 microns.

pMDIs and nebulisers are generally more efficient than dry powder formulations since approaches which use dry powders tend to suffer from the drawback that only a small portion of the powdered active ingredient is actually inhaled into the lungs.

Despite this drawback of lower efficiency, DPIs have the benefit that the energy required for aerosolisation of the formulation comes from the patient's own inhalation. This helps to avoid problems of poor hand-breath coordination (asynchrony) commonly associated with conventional pMDIs (see M. L. Levy et al. Prim Care Respir J. 2013, 22, 406-11).

Asynchrony has been observed in up to 58% of patients failing inhaler technique, and incorrect inhaler use is associated with poor asthma control and an increased risk of exacerbations (see V. Giraud and N. Roche Eur Respir J. 2002, 19, 246-51; H. Al-Jandali et al. Allergy Asthma Clin. Immunol. 2013, 9, 8; and A. S. Sundaresan et al. Allergy Asthma Proc. 2016, 37, 418).

This makes DPIs a useful approach for formulating inhalable active ingredients.

However, further to the known drawbacks described above in terms of potential performance and efficiency of DPIs compared with pMDIs and nebulisers, there are also increased difficulties in accurately testing the performance of DPIs in discharging the powdered medicaments. In particular, current methods of testing DPIs are highly limited in the degree of detail they are able to attain concerning the dynamics and geometry of the powder medicament plume discharged from the inhaler upon actuation.

The geometry and dynamics of the discharged plume are a significant factor in assessing the overall performance and efficacy of any inhaler. It may in particular have a substantial impact on the efficiency of delivery of medicament to the user.

Present methods for testing the plume characteristics of dry powder inhalers include for example impaction techniques, e.g. an Anderson cascade impactor (ACI) or a next-generation impactor (NGI). These techniques are based on drawing sample laden air through a stacked series of impaction stages, each comprising a collection surface designed to collect particles of a certain threshold inertia on the surface, whilst allowing the remainder of the particles to travel on to successive stages via an opening. The air is controlled to progressively accelerate as it travels through the different stages such that each collection surface is effectively selecting particles of ever decreasing inertia (i.e. mass). This allows a distribution of particles having a given inertia to be assessed within a discharged plume. However, this method is limited to analysis of the aerodynamic size of the particles within the plume and does not give an assessment of the geometric or dynamic characteristics of the plume.

Other methods for testing dry powder inhalers include electrostatic testing in which particles of a discharged dry powder plume are captured by an electrically charged collection plate, allowing rudimental aspects of the plume size and range for instance to be estimated. The precision achievable with such methods however is highly limited, and the attainment for instance of more detailed three-dimensional or cross-sectional analyses is not possible.

Current methods for testing pMDIs and nebulisers allow for high detail photographic or laser diffraction analysis of the discharged medicament spray. However these same methods are not directly transferrable to the analysis of DPIs due to the substantially different physical characteristics of a medicament in a powdered form compared to in an aerosolised form.

Absence of comparable plume characteristic data for dry powder inhalers is inhibiting efficient optimisation of these devices, since the impact upon powder discharge behaviour of any fine precision adjustments to the inhaler design is difficult to determine.

There is a need therefore for improved methods for testing dry powder inhalers to enable more detailed analysis of the characteristics of the discharged medicament powder plume.

Accordingly, the present invention provides a method of testing a dry powder inhaler comprising the steps of:
providing a dry powder inhaler (20) containing a dry powder formulation;
actuating the inhaler to discharge a dose of the dry powder formulation in the form of a dry powder plume (24);
illuminating the plume with a source of electromagnetic radiation (28);
capturing one or more images of a pattern of radiation reflected or diffracted by the electromagnetically illuminated plume (24); and
processing the images to determine one or more geometrical and/or dynamical characteristics of the discharged plume (24).

The present invention will now be described in detail with reference to the accompanying drawings, in which:

FIG. 1 schematically depicts an example testing method in accordance with the invention to obtain a longitudinal view of a discharged powder plume;

FIG. 2 schematically depicts a further example testing method in accordance with the invention to obtain a cross-sectional view of a discharged powder plume;

FIG. 3 schematically depicts the distal end of an airflow adaptor of an example inhaler tested in accordance with the present invention;

FIG. 4 schematically depicts the proximal end of an airflow adaptor of an example inhaler tested in accordance with the invention;

FIG. 5 schematically depicts a further view of the airflow adaptor of the example inhaler tested in accordance with the invention;

FIG. 6 schematically depicts a deagglomerator including a swirl chamber bypass port of the example inhaler tested in accordance with the invention;

FIG. 7 schematically depicts an isometric view of the example inhaler tested in accordance with the present invention;

The invention provides a method of testing an inhaler based on performing an optical analysis of a dry powder medicament plume discharged from the inhaler upon actuation. More particularly, embodiments of the invention comprise illuminating the dry powder plume with a source of electromagnetic radiation and capturing one or more images of a pattern of radiation reflected or diffracted by the illuminated plume. The images are subsequently processed to determine and/or analyse one or more geometric and/or dynamic characteristics of the plume.

Implementations of the invention allow for highly detailed information to be obtained on the discharge behaviour of the inhaler, informing for instance future improvements to the design or to the way in which the inhaler is to be used. The invention thus provides a contribution to the more overarching technical aim of achieving improvements in inhaler design and fluid dynamical performance.

The invention is based on capturing images of a pattern of radiation reflected or diffracted by the illuminated plume. By this is meant capturing an image of the reflection or diffraction pattern cast by the plume upon illumination by the source of electromagnetic (EM) radiation. Capturing an image of the reflection pattern may simply correspond with capturing an image of the illuminated plume.

Geometrical characteristics means characteristics pertaining to the shape or dimensions of the plume. Geometrical characteristics may include, but are not limited to, a length of the plume, a width of the plume, a cross-sectional area of the plume at a particular distance along its length and/or the cross-sectional area as a function of distance along the plume length, as well as powder density or concentration distribution across the plume volume.

Dynamical characteristics means characteristics pertaining to the dynamics or mechanics of the plume as a physical system. Dynamical is intended to be understood synonymously with dynamic. Dynamical characteristics may include, but are not limited to, an envelope velocity of the plume (i.e. a velocity of the plume, taken as a whole), a direction of movement of the plume, a dispersion rate of the plume, and particle velocities within the plume.

Figure 1:
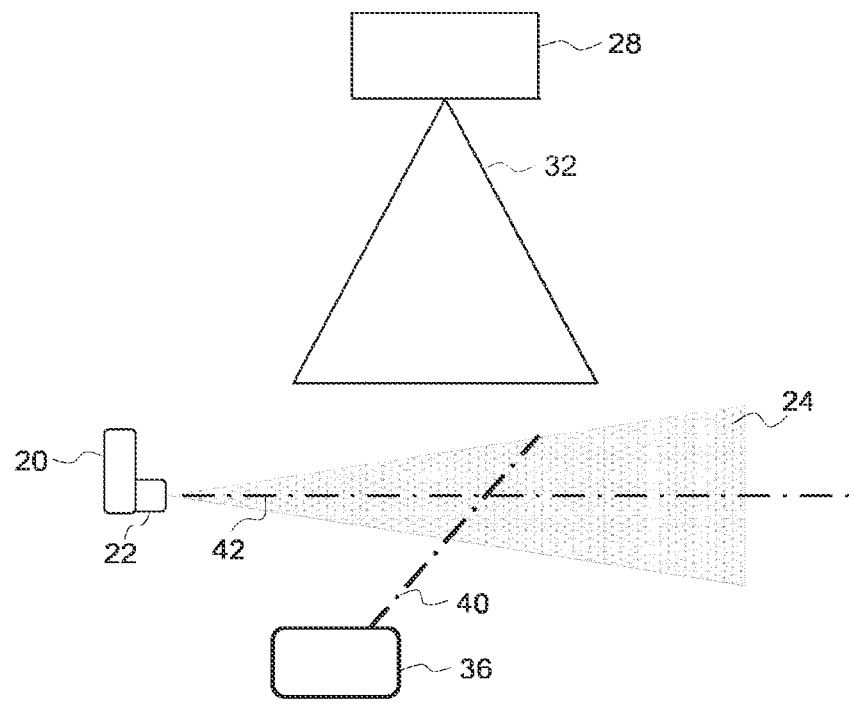
Figure 2:
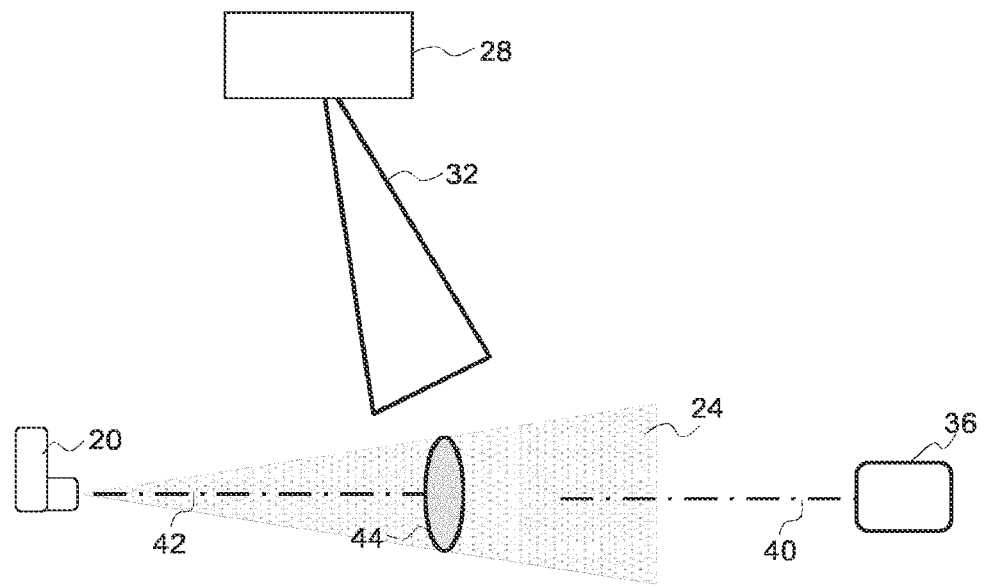
Figure 3:
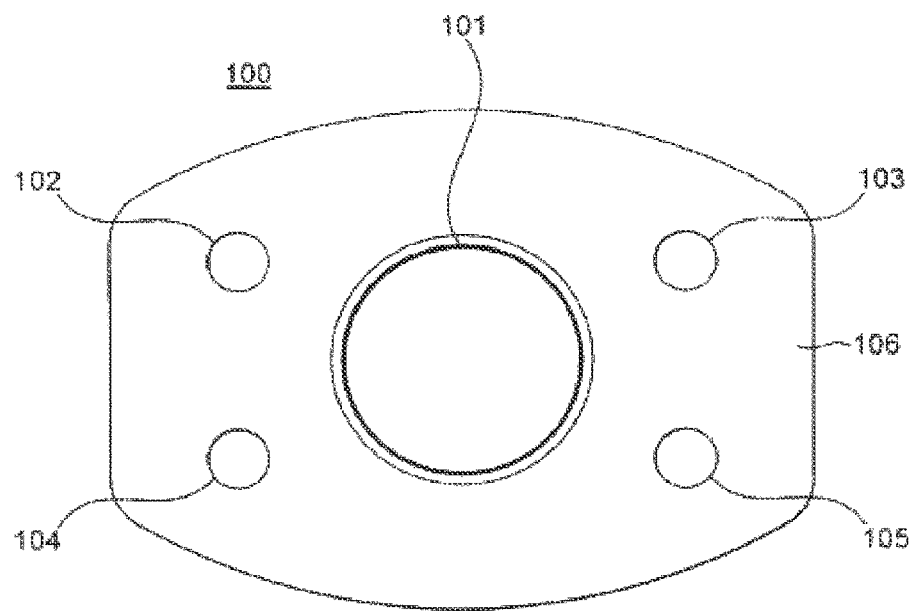

FIGS. 1 and 2 schematically depict execution of respective first and second example testing methods in accordance with the invention.

FIG. 1 shows execution of an example testing method configured for capturing and analysing characteristics of a discharged plume as viewed along a longitudinal axis 42 of the plume. An example inhaler 20 is actuated to discharge from a mouthpiece 22 a dose of medicament in the form of a dry powder plume 24. The plume is schematically depicted in FIG. 1 by means of a triangle representing a general shape of an outer envelope of the plume. Axis 42 represents a central axis of the outer envelope shape of the plume, indicating an axis of orientational alignment or directionality.

Outer envelope means the outer profile (i.e. outline) of the plume, taken as a whole. The central axis defines a line of directionality of the plume in the sense of a direction in which the powder plume is, taken as a whole, moving. Accordingly, the outer envelope shape of the discharged plume 24 has a central axis 42 defining an angular orientation of the discharged plume, and wherein the method comprises analysing said angular orientation of the plume. Thus, the present invention also comprises analysing a cross-sectional area 44 of an outer envelope shape of the discharged plume 24 at a given distance from a source of discharge of the plume, and optionally wherein said source of the discharge is defined as a distal end of a mouthpiece 22 of the inhaler 20.

Upon actuation of the inhaler 20 and discharge of the dry powder plume 24, a laser 28 is controlled to direct a laser light output 32 (i.e. EM radiation) onto the discharged power plume 24. In the present example, the laser light output is generated or optically processed so as to provide a spatially expansive or diverging beam (spatially extended in one or both dimensions orthogonal to a propagation direction) across the plume in the form of a sheet of light. Such an extended light sheet may enable a large region (or even the totality) of the plume to be illuminated and accordingly imaged for analysis. In particular examples, the laser 28 may be a FireFLY laser.

The laser 28 may be a visible light laser or may be a non-visible light laser such as for instance an infrared laser, ultraviolet laser, X-ray laser, or gamma-ray laser. The term should also be understood as covering masers.

Although a laser light source 28 is provided in the particular example of FIG. 1, it is to be understood that in this or any other example, the light source may be replaced by any suitable source of electromagnetic radiation. This may comprise a source of visible light or may be a source of a different form of electromagnetic radiation, such as infrared, microwaves, ultraviolet, x-rays or gamma rays for instance. Accordingly, the term images is to be construed broadly, as encompassing images formed through illumination by radiation of any region of the electromagnetic spectrum.

Concurrently with discharge and illumination of the dry powder plume 24, a high speed camera 36 is controlled to capture a plurality of images in succession of the pattern of laser light reflected or diffracted by the illuminated plume. The images are preferably captured as a plurality of images in series. The camera 36 may be configured to capture images recurrently at a frequency of 500 Hz for example. The images may be captured using high-speed photography techniques.

By capturing a plurality of images at regular intervals, details on the dynamics of the plume can be derived, including for instance internal dynamics of the particles within the plume as well as the dynamics of the overall plume itself, e.g. velocity, acceleration, dispersion rate.

Increased frequency in the image capturing leads to a greater detail in the obtainable analysis of the plume dynamics. Higher frequencies are therefore typically preferable. In particular examples, the images may be captured at regular intervals at an interval frequency of from 300 to 1,000 Hz In preferred examples, the images are captured at a frequency of at least 500 Hz. It has been found by the inventors that an image capture frequency of at least 500 Hz provides a particularly beneficial balance between high detail in the dynamical analysis while not placing overly high demand upon any computing resources required to process the images.

The camera 36 may be configured to capture diffraction patterns generated by illumination of the particles of the plume 24 by the laser light 32. In this case, the method may be a form of laser diffraction technique, wherein the pattern of diffraction generated by the plume is captured in an image and used to determine or analyse the geometrical and/or dynamic properties of the plume, including for instance density or concentration distribution.

Axis 40 illustrates a direction of focus of the camera 36, for instance the axis extending normally with respect an imaging plane of the camera. In this example, configured for capturing a longitudinal view of the discharged dry powder plume 24, the axis of focus of the camera is oriented approximately perpendicularly with respect to the axis of orientation (central axis) 42 of the plume 24.

Although a high speed camera is provided for capturing images in the particular example of FIG. 1, in further examples any suitable form of image capture device may be used which for instance comprises one or more elements sensitive to the respective band of the electromagnetic spectrum used to illuminate the plume. This may be a non-high-speed camera or a different variety of photosensitive device for instance. A device specifically configured for capturing diffraction patterns generated by laser illumination of the particles of the plume may also be used for instance.

Upon capturing the images, the images are processed to thereby determine and analyse one or more geometric and/or dynamic characteristics of the examined dry powder plume 24. This analysis may be performed by dedicated analysis software executed on a suitable computer device. Alternatively a dedicated image processor may be used to process the images and output analysis results.

Processing of the images of the longitudinal view of the powder plume captured in the method of FIG. 1 may typically enable determination (for each image) of at least: the orientation of the plume central axis 42 (relative to a given reference axis, such as an axis of a portion of the inhaler 20, or an absolute horizontal or vertical axis for instance), the angle of the cone defined by the plume outer envelope, the width of the plume at different points along its longitudinal length, and a length of the plume.

The central axis can be derived by finding a line which defines a median point across the width of the captured plume pattern.

The angle of the cone defined by the plume outer envelope (the angular extent of the cone) can be derived by finding the angular displacement between two lines defining the angular boundaries of the plume. These angular boundary lines might be chosen for instance so that a certain minimum percentage of the total plume area or captured volume is within the lines, e.g. 90%.

The plume width may be defined as a linear distance between these two boundary lines.

The method may comprise determining an angle of deviation of the central axis 42 of the discharged plume 24 with respect to an axis of orientation of the mouthpiece 22, i.e. the axis extending parallel to an inner conduit defined by the outer walls of the mouthpiece.

This angle of deviation may be a relevant factor in the performance or efficiency of the device. For instance if the angle of deviation of the plume 24 is particularly high, this may mean that the medicament is being incorrectly directed, for instance downward into the throat rather than directly along the airway for delivery to the lungs. This information may be used for instance to refine the design in the future or to change the way the device is used or configured. Accordingly, the dry powder inhaler 20 preferably comprises a mouthpiece 22, and wherein the method comprises determining an angle of deviation of said central axis 42 of an outer envelope of the discharged plume 24 with respect to an axis of orientation of the mouthpiece.

The processing of the images and generation of analysis data may be performed simultaneously with capturing of the images or alternatively may be performed subsequently.

Processing of the images to thus derive indications or measures of the geometrical or dynamical characteristic(s) can be performed using any suitable image analysis procedure. This may be computer implemented, for instance by means of image analysis software executed on a computer. Alternatively it may according to further examples be implemented by a suitable image processor.

Oxford Lasers Envision Patternate software is one example of suitable software which may be used to extract plume geometry and dynamics information from the captured images. The software can be purchased from Oxford Lasers.

The Oxford Lasers EnVision Patternate software enables extraction from captured images of at least the following characteristics: plume cone angle, plume width, plume height, spray pattern ellipticity, spray pattern size, and spray event duration.

The EnVision software performs characterisation on a single image or can combine a sequence of images of the plume to form a composite image and then measures the cone angle, direction, plume geometry and other user-definable parameters.

A further piece of software which may in accordance with examples be used to extract plume geometry and dynamics information from the captured images is Oxford Lasers VidPIV software. This software may be purchased from Oxford Lasers.

The Oxford Lasers VidPIV software permits extraction in particular of plume velocity information, and allows an average velocity of the plume to be derived, as well as a full velocity vector map of the plume over time.

The obtained set of consecutive images may be processed to form a computational fluid dynamical model of the plume. This may be used to provide highly detailed information on a range of aspects of the plume behaviour throughout the duration of the discharge process including for instance aspects of its geometry, density and mechanics at different moments in time, as well as how these properties change as a function of time.

In particular examples, the inhaler 20 may be actuated in a vacuum chamber or an air flow chamber. This may improve accuracy or detail of the obtained analyses of plume geometry or dynamics. By conducting the test in a vacuum, the plume is unaffected by environmental (fluid) conditions for example.

FIG. 2 shows execution of an example testing method of the invention, configured for capturing and analysing characteristics of a discharged plume 24 across a given cross-section 44 at a given distance from a source of discharge of the plume. As in the example of FIG. 1, a test inhaler 20 is actuated to discharge a dose of medicament in the form of a dry powder plume 24. Again, the plume is illustrated schematically by a triangle shape, representing an outer envelope shape of the plume. Axis 42 represents a central axis of the envelope shape, and indicates a general angle of orientation of the plume 24. All terms may be understood as defined above.

Upon actuation of the inhaler 20 and discharge of the plume 24, a laser 28 is controlled to direct a source of laser light 32 across at least a particular cross-sectional region 44 of the illuminated plume 24 at a given distance from a source of discharge of the plume (in this case a distal end of the mouthpiece 22). The given distance may be selected in advance, typically 3 cm or 6 cm. In particular examples, the distance may be 3 cm. Testing at this distance is standard within the field of inhaler testing.

As in the example of FIG. 1, the light output 32 of the laser 28 may be generated or optically processed so as to provide an approximately planar sheet of light. This may be directed (as shown in FIG. 2) radially across the width of a particular cross-sectional region 44 of the plume 24.

Concurrently with discharge and illumination of the plume 24, a high-speed camera 36 is controlled to capture a series of images in quick succession (for instance at a frequency of at least 500 Hz). Axis 40 indicates a direction of focus of the camera 36. In this particular example, configured for capturing a cross-sectional view or impression (e.g. as created by a diffraction pattern) of the plume 24, the imaging plane of the camera is aligned in parallel with the direction of orientation (as indicated by central axis 42) of the dry powder plume 24. This enables the camera to capture the reflection or diffraction pattern cast by the particular cross-section 44 of the plume being illuminated by the laser 28.

As in the previous example, use of a high-speed camera is indicated for the particular example illustrated in FIG. 2. However, this is not essential, and in further examples any suitable image or light pattern capturing device may be used. A device configured specifically for capturing diffraction patterns may for instance be used in accordance with one or more examples.

Upon capturing the images, the images are processed to thereby determine and analyse one or more geometric and/or dynamical characteristics of the dry powder plume 24. This analysis may be performed by dedicated analysis software executed on a suitable computer device. Alternatively a dedicated image processor may be used to process the images and output analysis results. Suitable example software is described above.

Processing of the images of the cross-sectional view 44 of the powder plume 24 captured in the method of FIG. 2 may typically enable determination of (for each image) at least: a radius of the plume cross section in each angular direction, maximal and minimal dimensions of the plume cross-section, a total area of the cross-section, and a concentration (or density) distribution of the powder across the cross-section 44.

The cross-sectional area of the plume may provide an indication of deagglomeration performance of the inhaler. For example, a smaller cross-section may typically indicate a greater average powder density within said cross-section 44. Where there is a greater density of powder, there is typically a greater rate of inter-particle collisions which lead to break-up (i.e. deagglomeration) of agglomerations of the powder medicament. For best medical results, it is preferable that the powder contains a high percentage fine particle fraction. Hence, by analysing cross-sectional area, an indication of post-discharge deagglomeration performance is attainable.

The cross-sectional area may also be relevant for other reasons. For instance, a narrower cross-section may in particular cases be preferable for instance to provide more directional discharge of the powder into a user's airway. A wider or more dispersed plume may for instance be more prone to spreading into the user's throat or mouth.

The concentration distribution of the powder may provide information relevant to the medical efficiency of the device. For example, a greater concentration of particles at a more central region may indicate a more directionally focussed plume. For instance, a plume having a high central concentration may be less prone to substantial radial dispersion as it travels toward the user's airway.

Additionally, a more centrally concentrated plume may exhibit greater deagglomeration action after discharge from the inhaler due to increased particle interactions.

Powder concentration distribution means powder density distribution across the given cross-section 44. By this is not meant the density of the material itself, but rather the concentration of the powder, i.e. the number of powder particles per unit area, as a function of position across the cross-section in question. The concentration distribution may be in the form of a set of values of powder density or concentration at different points across the imaged cross-section 44. Thus, the present invention comprises determining a powder concentration distribution across a given cross-section 44 of the discharged plume 24 at a given distance from a source of discharge of the plume.

In accordance with one or more examples, a number of different cross-sections 44 may be imaged at different distances from the mouthpiece 22, and in these cases, the processing of the images may enable determination of the above properties for each of the imaged cross-sections.

The processing of the images and generation of analysis data may be performed simultaneously with capturing of the images or alternatively may be performed subsequently.

Methods for processing the images to derive these properties have been described above.

It is to be noted that any features or possible variations described in relation to one of the two examples (of FIG. 1 and FIG. 2) are to be understood as equally applicable to the other of the two examples. Features of each may be combined or exchanged to provide further examples.

Benefits of the testing method of the present invention in providing instructive analysis of the geometric and dynamic characteristics of the generated powder plume may become more apparent through examination of a particular example of its application.

One example of the use of the method will now be described in detail, in relation to a particular example inhaler device tested in accordance with the method. A brief outline of the features and characteristics of the inhaler tested will first be presented, before describing the results of testing. A more detailed description of the particular inhaler tested may be found in WO 2011/054527.

The inhaler tested is a breath-actuated dry powder inhaler comprising an airflow adaptor, the airflow adaptor comprising: a first conduit having a proximal end and a distal end, wherein the proximal end allows fluid communication from a deagglomerator outlet port to the distal end of the conduit, and wherein the airflow adaptor further comprises at least one second conduit for allowing air to flow from a proximal end of the adaptor to a distal end of the adaptor independently of the airflow in the conduit when a breath induced low pressure is applied to the distal end of the airflow adaptor. Furthermore, the ratio of the sum of the cross-sectional areas of the at least one second conduit to the cross-sectional area of the first conduit is such that when a breath induced low pressure is applied to the distal end of the airflow adaptor from about 20% to about 50% of the resulting airflow is through the at least one second conduit.

The at least one second conduit of the airflow adaptor hence allows air to by-pass the deagglomerator, thereby altering the dynamics of the generated powder plume.

FIG. 3 shows a distal end of the airflow adaptor 100. The airflow adaptor comprises a conduit 101 with a first circumferential flange 106.

The airflow adaptor also comprises means for allowing air to flow from a proximal end of the adaptor to a distal end of the adaptor independently of the airflow in the conduit when a breath induced low pressure is applied to the distal end of the airflow adaptor. The means for thus allowing air to flow independently of the conduit are in the form of four apertures 102, 103, 104, 105 in the first circumferential flange 106. In alternative embodiments there may be other numbers of apertures.

Figure 4:
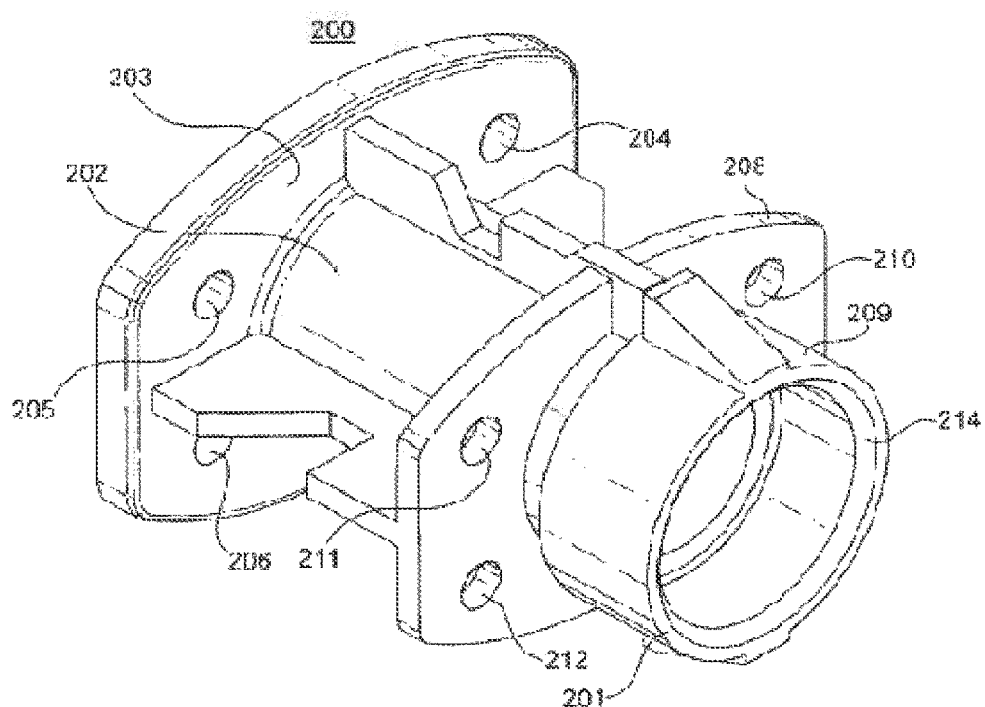

FIG. 4 shows a view of the proximal end 201 of the airflow adaptor 200 in a partially constructed state. The airflow adaptor comprises a conduit 202 with a first circumferential flange 203. The conduit shown has a circular cross-section; however, it may have any cross-sectional shape.

The airflow adaptor also comprises means for allowing air to flow from a proximal end of the adaptor to a distal end of the adaptor independently of the airflow in the conduit when a breath induced low pressure is applied to the distal end of the airflow adaptor. The means are in the form of four apertures 204, 205, 206 (fourth not shown) in the first circumferential flange 203. Other numbers of apertures may also be provided.

The airflow adaptor 200 shown in FIG. 4 further comprises a second circumferential flange 208. The second circumferential flange also comprises four apertures 210, 211, 212 (fourth not shown).

The proximal end 209 of the conduit 202 allows fluid communication from a deagglomerator outlet port to the distal end of the conduit. In particular, the airflow adaptor 200 shown in FIG. 4 has a mating surface 214 for mating with the outlet port of a deagglomerator outlet port. Preferably, they mate such that, during use, air will not flow across the mating surface. In certain other embodiments, the outlet port and the airflow adaptor may be a unitary structure.

Figure 5:
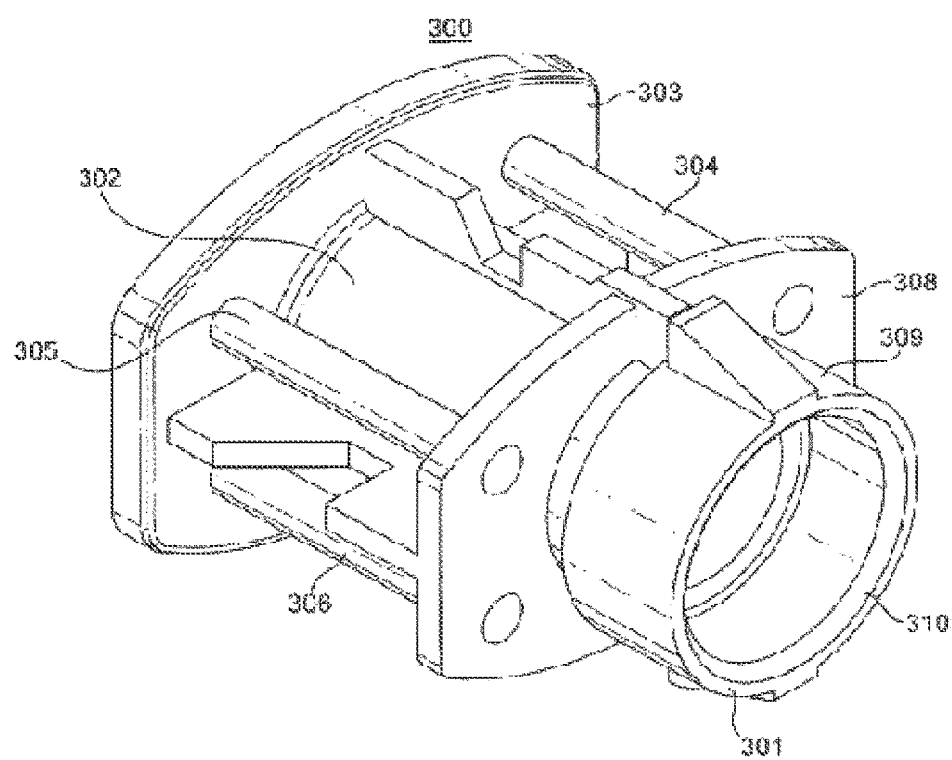
Figure 6:
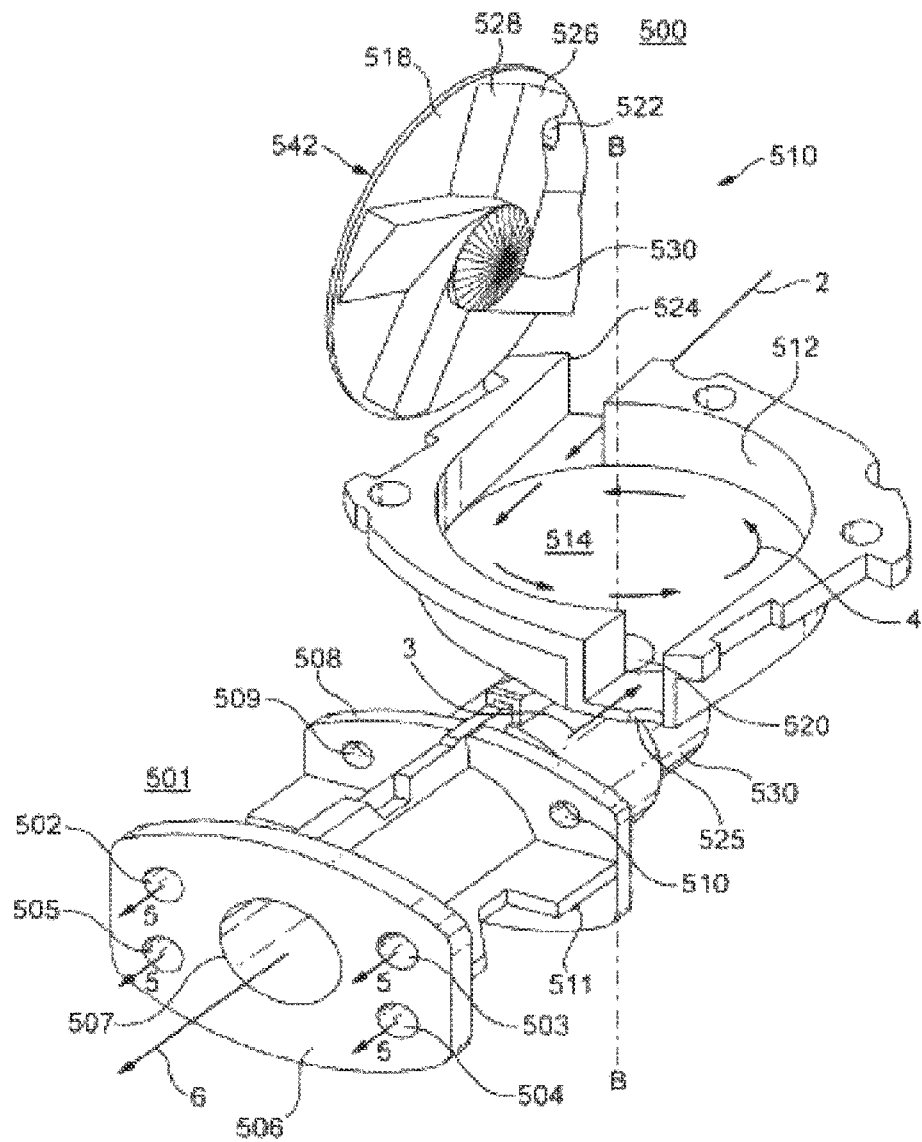
Figure 7:
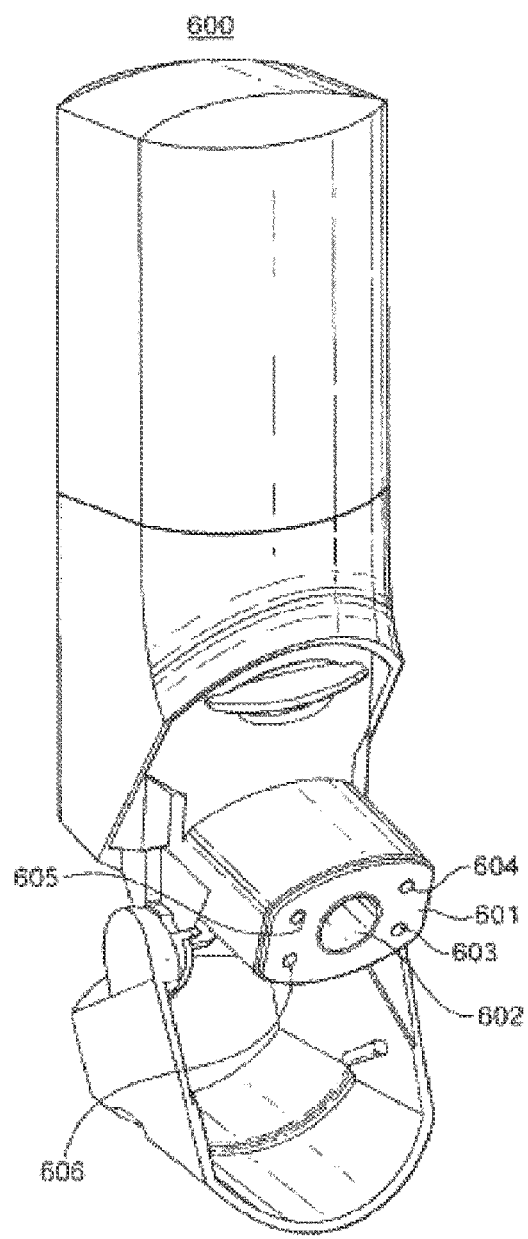
Figure 8:
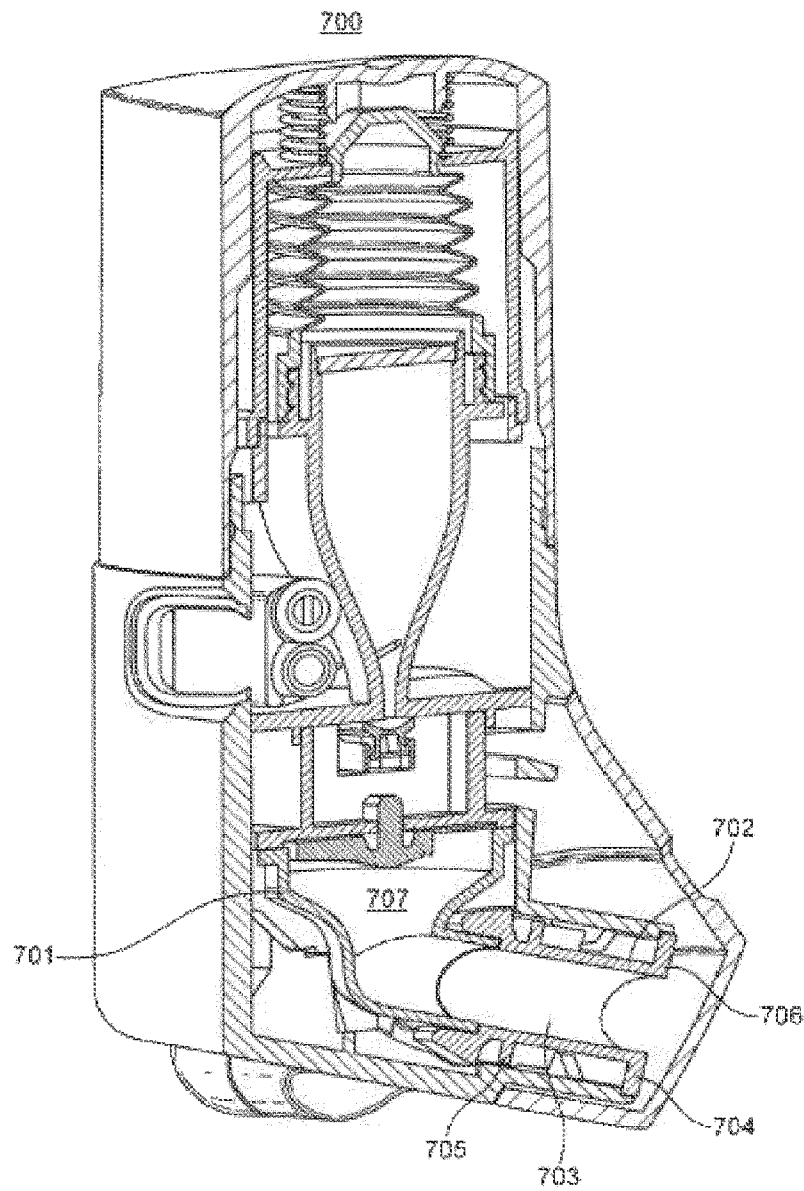
FIG. 8 shows a cross-sectional view of the example inhaler tested in accordance with the invention.

FIG. 5 shows a view of the proximal end 301 of the airflow adaptor 300 in a fully constructed state. In this figure, four second conduits 304, 305, 306 (fourth not shown) can be seen, running from the second circumferential flange 308 to the first circumferential flange 303. These provide means for allowing air to flow from a proximal end of the adaptor to a distal end of the adaptor independently of the airflow in the conduit when a breath induced low pressure is applied to the distal end of the airflow adaptor The airflow adaptor may be moulded from any suitable polymeric material, including for instance polypropylene and acrylonitrile butadiene styrene.

FIG. 6 shows a deagglomerator 500 coupled with the airflow adaptor 501. The deagglomerator 500 comprises: an airflow adaptor 501 providing fluid communication between the outlet port 530 and a region exterior to the deagglomerator; an inner wall 512 defining a swirl chamber 514 extending along an axis B from a first end 518 to a second end 520; a dry powder supply port 522 in the first end 518 of the swirl chamber 514 for providing fluid communication between a dry powder delivery passageway of an inhaler and the first end 518 of the swirl chamber 514; at least one inlet port 524, 525 in the inner wall 512 of the swirl chamber 514 adjacent to the first end 518 of the swirl chamber 514 providing fluid communication between a region exterior to the deagglomerator and the first end 518 of the swirl chamber; an outlet port 530 providing fluid communication between the second end 520 and the airflow adaptor 501; and at least one swirl chamber bypass port 502, 503, 504, 505.

The at least one swirl chamber by-pass port 502, 503, 504, 505 allows air to flow (shown by arrows labelled 5) from a proximal end of the airflow adaptor to a distal end of the airflow adaptor 501 independently of the swirl-chamber 514 when a breath-induced low pressure is applied to the distal end of the airflow adaptor. The breath induced low pressure at the distal end of the airflow adaptor 501 also causes air to flow into the swirl chamber 514 through the dry powder supply port 522 and the at least one inlet port 524, 525. The combined airflow (arrow 4) leaves the airflow adaptor 501 through the conduit 507 (shown by arrow 6).

The at least one swirl chamber bypass port shown in FIG. 6 is in the form of four apertures 502, 503, 504, 505 in a first circumferential flange 506 of a conduit 507 of the airflow adaptor 501. The airflow adaptor 501 shown in FIG. 6 further comprises an optional second circumferential flange 508 which also comprises four apertures 509, 510, 511 (fourth not shown). When present, in use, the apertures 509, 510, 511 (fourth not shown) in the second circumferential flange 508 also form part of the swirl chamber bypass port.

The airflow adaptor shown in FIG. 6 is the airflow adaptor shown in FIG. 5. The second conduits of FIG. 5 perform the function of swirl chamber bypass ports. Indeed any of the airflow adaptors described herein when combined with a deagglomerator as described above provide a swirl chamber bypass port.

The ratio of the sum of the cross-sectional areas of the at least one swirl chamber bypass ports to the cross-sectional area of outlet port is such that that when a breath induced low pressure is applied to the distal end of the airflow adaptor from about 20% to about 30% of the resulting airflow is directed through the at least one swirl chamber bypass port.

FIG. 7 shows the external appearance of the breath-actuated dry powder inhaler 600 tested. The breath-actuated dry powder inhaler comprises an airflow adaptor 601 having a conduit 602 and four second conduits 603, 604, 605, 606. In this instance, the conduit 602 and the second conduits 603, 604, 605, 606 have circular cross-sections.

FIG. 8 shows the breath-actuated dry powder inhaler 700 comprising the deagglomerator 701 and the airflow adaptor 702.

The airflow adaptor 702 comprises a conduit 703 with a first circumferential flange 704 comprising four apertures (not shown). The airflow adaptor further comprises a second circumferential flange 705 also comprising four apertures (not shown). The apertures in the first and second circumferential flanges perform the function of swirl chamber bypass ports (by performing the function of the at least one second conduit(s)). Accordingly, in use, a breath-actuated low pressure at the distal end 706 of the airflow adaptor 702 causes air to flow through the apertures (not shown) in the first 704 and second 705 circumferential flanges. The breath-actuated low pressure at the distal end 706 of the airflow adaptor 702 also causes air to entrain medicament and deliver it to the swirl chamber 707 via a supply port.

The above described inhaler (henceforth referred to as a 'high-flow inhaler') has been tested using an embodiment of the testing method of the present invention. For comparison, a second inhaler (henceforth referred to as a 'standard inhaler') was also tested, this being similar to the first except that the airflow adaptor does not comprise the four second conduits 603, 604, 605, 606 acting as swirl chamber by-pass conduits. Accordingly, when a breath induced low pressure is applied to the distal end of this second inhaler's airflow adaptor, all of the resulting airflow is directed through the swirl chamber.

Each of the two inhaler varieties was tested using each of the two example methods described above (with reference respectively to FIGS. 1 and 2). In each case, two randomly selected sample inhalers of that variety were tested in accordance with the particular method concerned.

Figure 9:
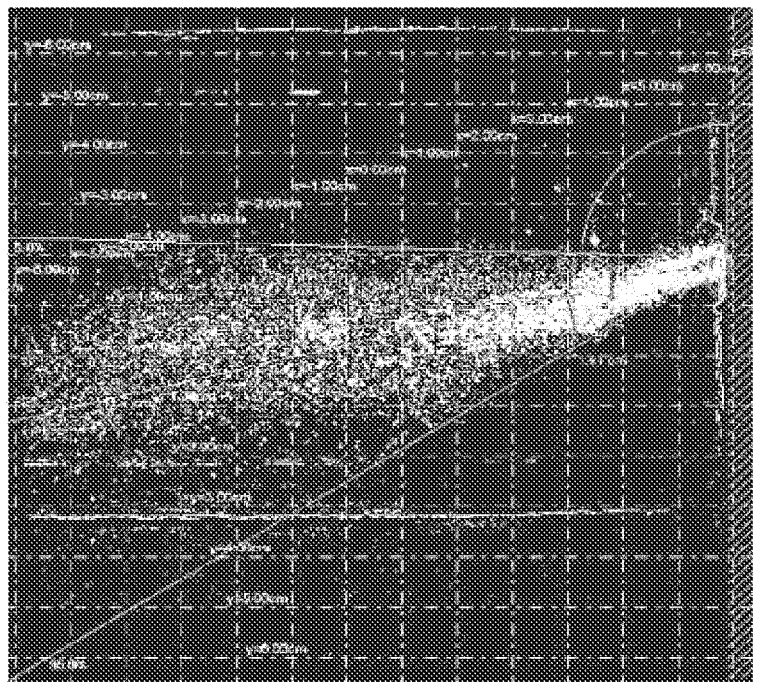
FIGS. 9-12 show an image of a powder plume captured in accordance with the invention.
Figure 10:
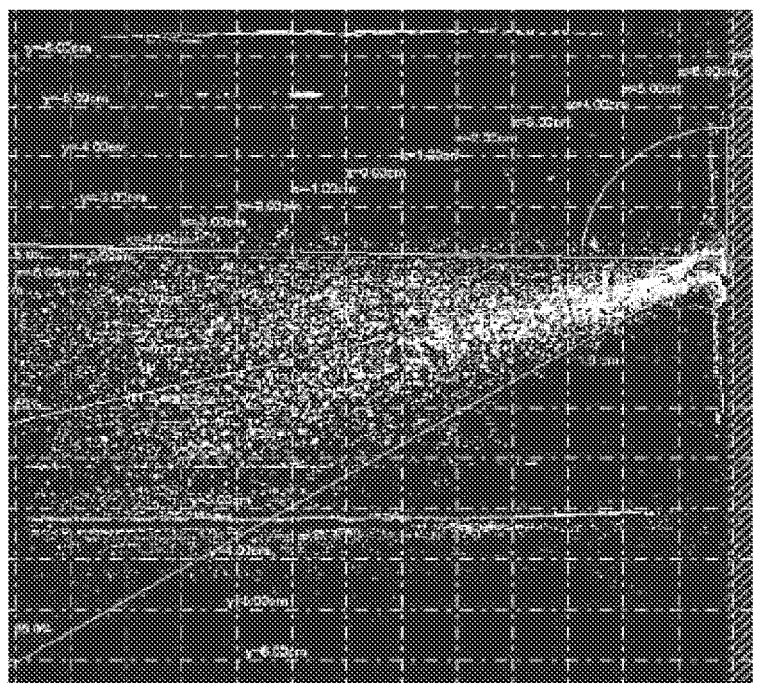

FIGS. 9 and 10 show plume pattern images captured for each of two sample standard inhalers (i.e. without the by-pass conduits) tested in accordance with the longitudinal view test illustrated in FIG. 1.

Table 1 below sets out a summary of the results achieved for these two tests. In particular, the table details average values for an orientation of the discharged plume (i.e. orientation angle of a central axis of the plume) relative to the mouthpiece of the inhaler, as well as cone angle of the outer envelope shape of the plume and total length and width of the plume. The mouthpiece in this case was oriented with its outflow aligned horizontally.

TABLE 1

Longitudinal view test results for standard inhaler

|  | Orientation (°) | Cone Angle (°) | Cone width (cm) at 3 cm from mouthpiece | Length (cm) |
|---|---|---|---|---|
| Average | 104.96 | 35.72 | 1.57 | 10.65 |
| SD | 0.71 | 1.85 | 0.2 | 0.66 |

The results of the test reveal some surprising features of the discharged plume geometry. In particular, it can be seen from both FIGS. 9 and 10 and from the values in Table 1 that despite the horizontal alignment of the mouthpiece, the discharged plume is oriented with a downward incline. It was expected by the inventors that the test would reveal that the plume was emitted approximately horizontally, with any drop being commensurate only for example with the effects of gravity. However, the results reveal a significant declination of the plume alignment. In particular, average angle of a central axis of the plume with respect to vertical was found to be 104.96° (where 90° would have indicated perfect horizontal alignment). There is hence a misalignment in this case of approximately 15°.

Such an angular misalignment may have tangible effects on the medical efficiency of the inhaler in delivering the powdered medicament. For example, a greater angle of deviation may lead to less efficient delivery of the medicament to a user's airway, for instance by allowing some of the powder to be misdirected to undesired areas such as the throat or mouth.

Figure 11:
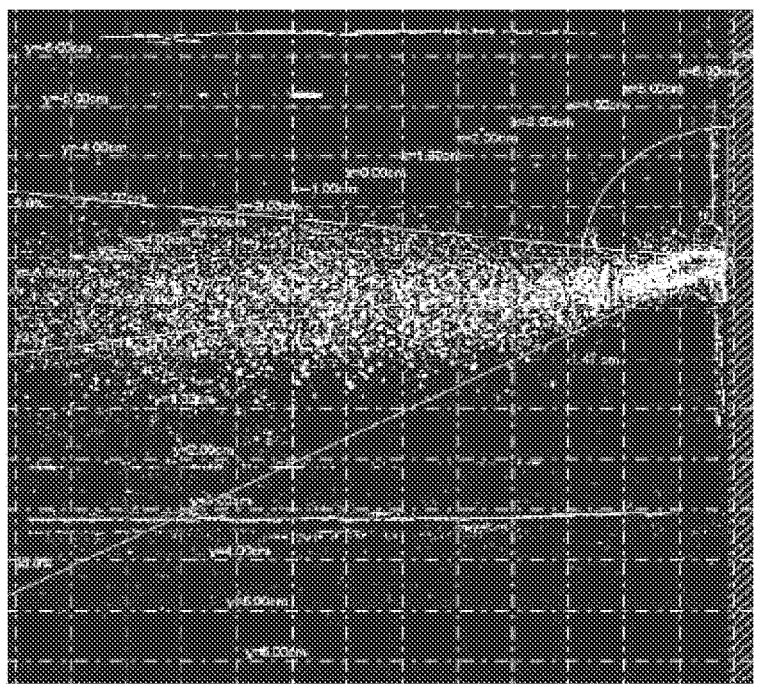
Figure 12:
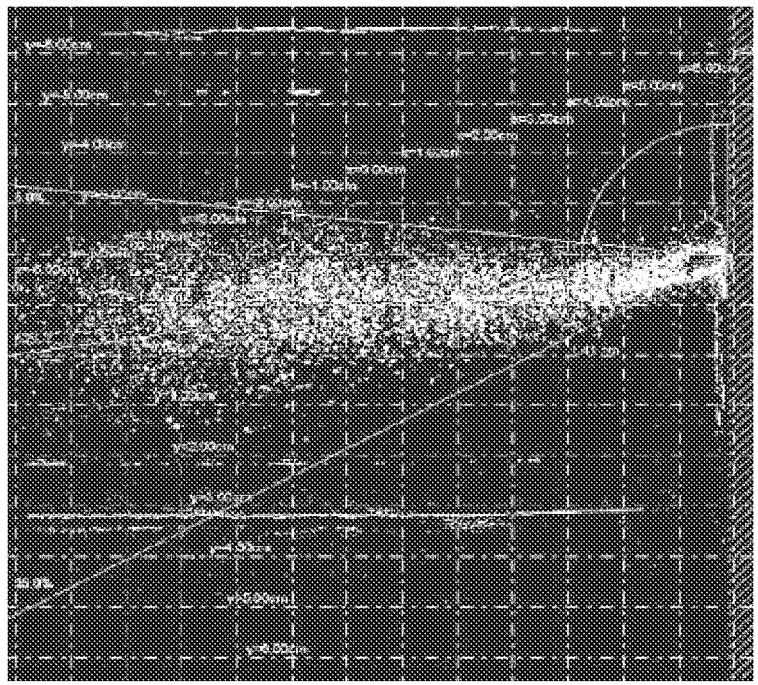

The results for the standard inhaler may be compared with those achieved for the high-flow inhaler. FIGS. 11 and 12 show plume pattern images captured for each of two example high-flow inhalers (i.e. with the by-pass conduits) and Table 2 below sets out a summary of the results achieved for these two tests. The same quantities were measured as in the above described tests for the standard inhalers and, again, the mouthpiece was oriented with its outflow aligned horizontally.

TABLE 2

Longitudinal view test results for the high-flow inhaler

|  | Orientation (°) | Cone Angle (°) | Cone width (cm) at 3 cm from mouthpiece | Length (cm) |
|---|---|---|---|---|
| Average | 97.73 | 33.52 | 1.41 | 11.18 |
| SD | 1.91 | 1.94 | 0.08 | 0.17 |

It is apparent both from the captured images shown in FIGS. 11 and 12 and from the numbers in Table 2 that the plume characteristics for the high-flow inhaler are significantly different to those for the standard inhaler.

In particular, the angle of orientation of the plume for the high-flow inhaler is closer to horizontal. The average angle of the central axis of the plume from vertical was found to be 97.73°, i.e. deviating only approximately 8° from perfect horizontal alignment. This hence represents a reduction of approximately 7° in the angle of deviation of the plume from horizontal compared with the standard inhaler.

This hence provides an indication that the structural differences between the two varieties of inhaler significantly impact upon their fluid dynamical performance. It can be inferred from these tests in particular that the presence of the by-pass ports of the high-flow inhaler (described above in relation FIGS. 3-8) reduces the angle of deviation of the discharged powder plume from perfect horizontal alignment. Such results, achievable using the methods of the present invention provide a tangible technical contribution to the overall technical object of improving fluid dynamical performance and/or medical efficacy of inhalers.

Other results obtained using the longitudinal view tests are also notable. It may be seen for instance that the cone angle of the plume is smaller for the high-flow inhaler (at an average of 33.52°) than for the standard inhaler (having an average of 35.72°). This indicates that the structural differences in the high-flow inhaler also lead to a narrower or more focussed plume (something also revealed more clearly in the cross-sectional view tests, results of which are described below).

As noted above, a more focussed or less dispersed plume may have tangible effects on efficiency or performance of the inhaler, for instance enabling greater directionality of the plume, thereby allowing easier targeting of the powdered medicament directly toward the airway of the user, and potentially limiting misdirecting of the medicament into the throat or mouth. A more focussed plume may also increase so-called post-discharge deagglomeration action, wherein a particle-particle collision rate within the plume after ejection from the inhaler is increased due to the greater plume density. This leads to further deagglomeration of the powder, which improves medical efficacy of the medicament once delivered.

The reduction of cone angle is also reflected in the results for plume width for the respective Inhaler varieties, with the average plume width reducing from 1.57 cm (for the standard inhaler) to 1.41 cm (for the high-flow inhaler).

Figure 13:
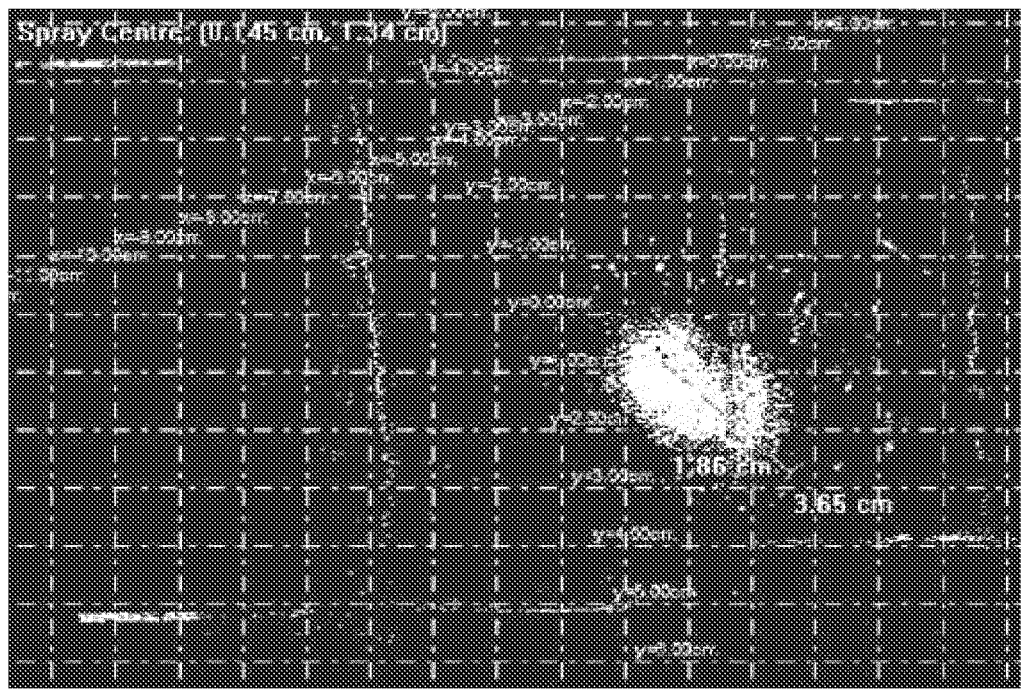
FIGS. 13-16 show an image of a cross-section of a powder plume captured in accordance with the invention.
Figure 14:
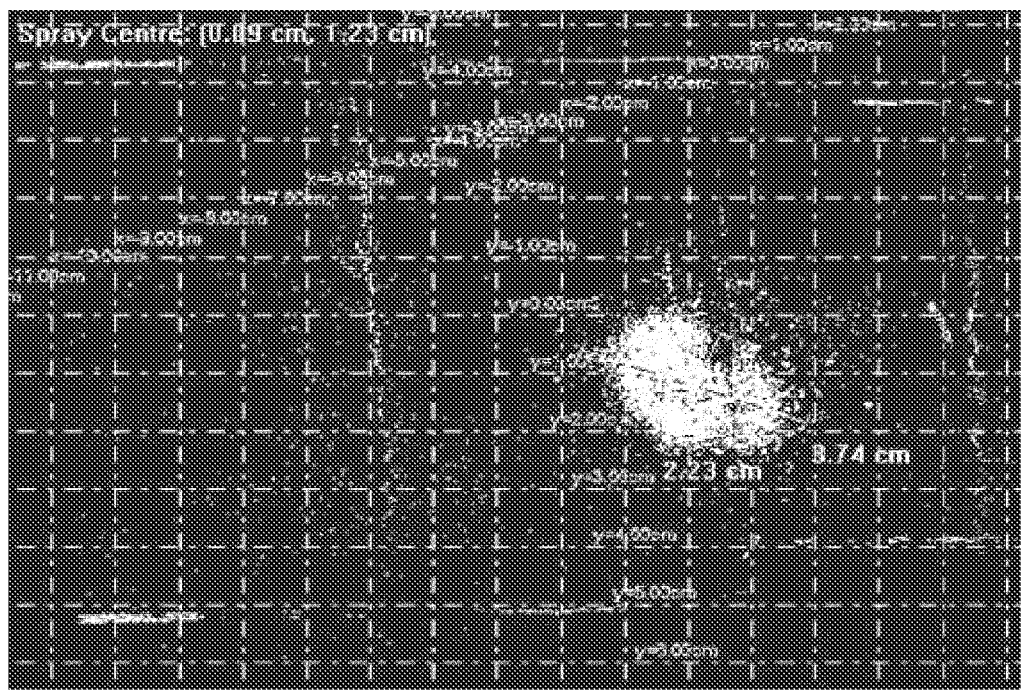

FIGS. 13 and 14 show plume pattern images captured for each of two example standard inhalers (i.e. without the by-pass conduits) tested in accordance with the cross-sectional view test illustrated in FIG. 2. The images capture a cross-section of the discharged plume at a distance of 3 cm from the inhaler mouthpiece Table 3 below details the numerical results for these tests, in particular setting out average values for a range of dimensional characteristics of the particular cross-section imaged.

TABLE 3

Cross-sectional view test results for standard inhaler

|  | Length of shortest diameter (cm) | Orientation of shortest diameter (°) | Length of longest diameter (cm) | Orientation of longest diameter (°) | Min/max ratio | Area (cm²) |
|---|---|---|---|---|---|---|
| Average | 2 | 62.02 | 3.72 | 37.08 | 1.87 | 6.16 |
| SD | 0.22 | 11.76 | 0.25 | 10.25 | 0.22 | 0.54 |

Two particularly notable results are those of total cross-sectional area (with an average value of 6.16 cm$^2$) and length of the longest diameter of the cross-section (average value of 3.72 cm).

Figure 15:
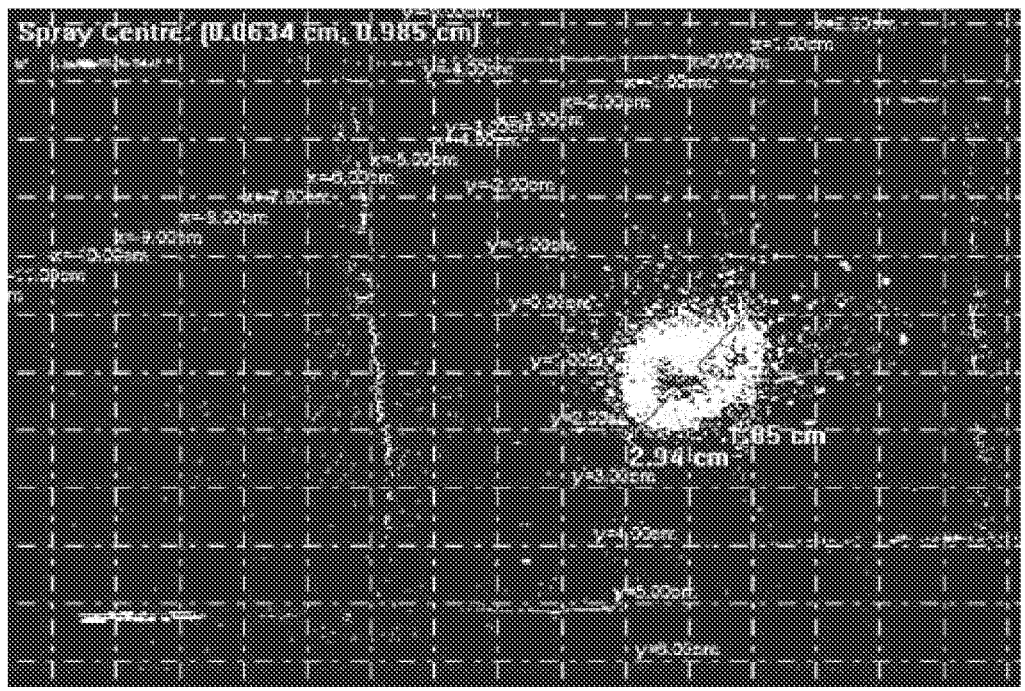
Figure 16:
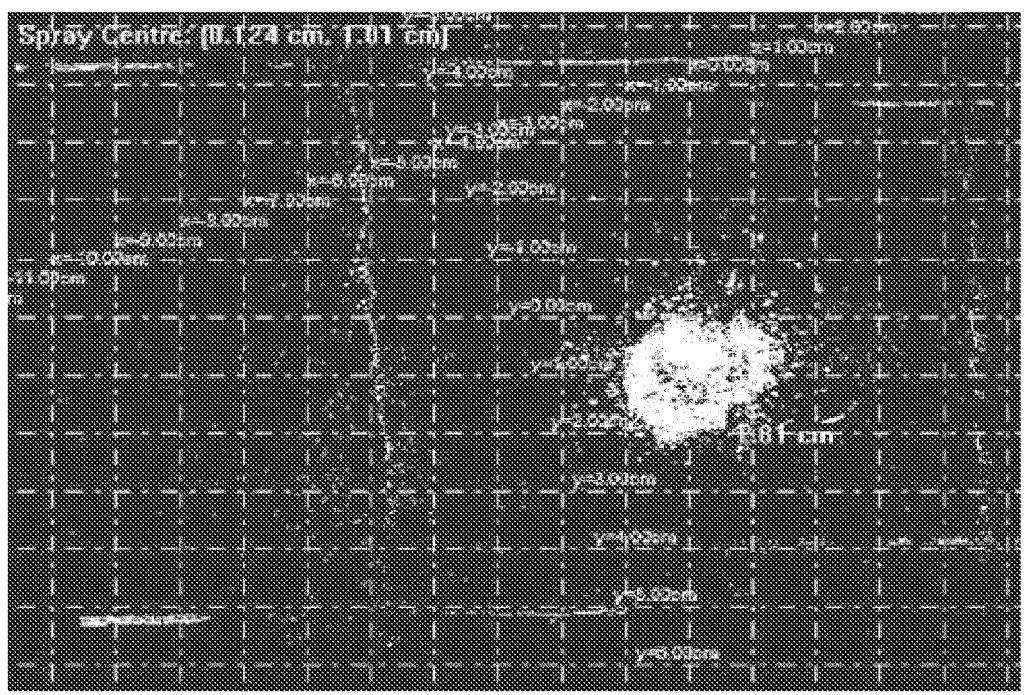

These results are notable by comparison with the corresponding results obtained for the high-flow inhaler. FIGS. 15 and 16 show plume pattern images captured for two example high-flow inhalers tested in accordance with the cross-sectional view test of FIG. 2. The images again correspond to cross-sections at a distance of 3 cm from the inhaler mouthpiece. Table 4 below details the average numerical results for the two tests.

TABLE 4

Cross-sectional view test results for high-flow inhaler

| | Length of shortest diameter (cm) | Orientation of shortest diameter (°) | Length of longest diameter (cm) | Orientation of longest diameter (°) | Min/ max ratio | Area (cm$^2$) |
|---|---|---|---|---|---|---|
| Average | 1.93 | 59.78 | 2.97 | 31.03 | 1.55 | 4.51 |
| SD | 0.21 | 15.56 | 0.17 | 14.98 | 0.08 | 0.59 |

It can be seen both from the images and Tables 3 and 4 that the average cross-sectional area for the high-flow inhalers is significantly less than the corresponding areas for the standard inhalers. In particular, the average area for the high-flow inhaler plumes decreases to 4.51 cm$^2$ compared to an average value of 6.16 cm$^2$ for the standard inhaler. This decrease in size of the cross-section is also reflected in the value for the length of longest diameter, which has an average value of 2.97 cm for the high-flow inhaler compared to 3.72 cm for the standard inhaler.

The smaller cross-sectional area for the high-flow inhaler may indicate a more concentrated or focussed plume. As noted above, this may also indicate a greater directionality of the plume, allowing for more efficient delivery of the powdered medicament to the user's airway, or may indicate increased post-discharge deagglomeration action.

In addition to the reduced cross-sectional area, another notable result is that of concentration distribution of the powder across the imaged cross-section. This property is reflected in the full-colour original images by a colour variation across the imaged cross-section (information not visible in the black-and-white versions of the images provided herein).

However, the colour distribution shows that for the high-flow inhaler plume, there is a significantly elevated powder density (or concentration) within a central region of the plume cross-section compared to more extremal regions. This indicates a more centrally focussed or concentrated plume, with central regions comprising a greater concentration of powder than outer regions.

This contrasts with the equivalent result for the standard inhaler, where the colour distribution, although indicating some elevated powder concentration within central regions, reveals a comparatively homogenous powder concentration distribution across the cross-section imaged.

It is to be noted that although the example testing method above is described specifically in relation to testing of two varieties of inhaler in particular, this is purely by way of illustration, and is not to be understood an implying any limitation on the scope of applicability of the testing method to any alternative dry powder inhaler.

It can be seen that example testing methods of the present invention enable technically relevant information concerning characteristics of the discharged medicament plume to be obtained. The results of this testing may furthermore be utilised in modifying or refining the design of an inhaler. By comparing results for two designs, it may be seen that a particular distinguishing feature or modification of one design leads to an advantageous effect upon the geometric or dynamical characteristics of the plume. These results may then be utilised in further design procedures to improve the design.

Accordingly, the present invention also provides a method of designing a dry powder inhaler 20, the inhaler being operable to discharge a dose of medicament in the form of a dry powder plume, the method comprising:

providing a first dry powder inhaler in accordance with a first design, the design intended to achieve a particular desired set of plume geometric and/or dynamic characteristics;

testing the dry powder inhaler 20 by means of a testing method defined in any preceding claim; and if necessary, adjusting the design of the first dry powder inhaler 20 based on results of said testing so as to better achieve the desired set of plume geometric and/or dynamic characteristics.

In particular, the method may comprises adjusting the design so as to minimise an angle of deviation of a central axis 42 of an outer envelope shape of the discharged plume 24 with respect to an axis of orientation of a mouthpiece 22 of the inhaler, and optionally wherein the mouthpiece defines a source of discharge of the plume. The mouthpiece may define a source of discharge of the plume.

As noted above, a large angle of deviation may be medically disadvantageous, leading to delivery of the powder to regions where it is not required, such as the throat or mouth. By minimising this angle, such deficiencies in the performance of the device may be ameliorated.

Additionally or alternatively, the method may comprise adjusting the design so as to reduce a cross-sectional area 44 of an outer envelope shape of the discharged plume 24 at a given distance from a source of discharge of the plume.

As noted above, reducing the cross-section may increase deagglomeration action within the plume as it exits from the inhaler. This leads to finer breakdown of the powder and improved medical efficacy. Reducing the cross-section may also enable greater directionality in the projected plume, allowing for more focussed delivery of the power directly into the airway of the user.

The method may, additionally or alternatively, comprise adjusting the design so as to alter a concentration distribution of the powder across a given cross-section of the plume, the cross-section being located at a given distance from a source of discharge of the plume. In particular examples, the design may be adjusted so as to increase a concentration of the powder within a central region of the cross section, proximal to a central point or centroid of the cross section.

As noted above, increased concentration within a central region may improve medical efficacy, for example by rendering a more directionally focussed plume, or by increasing post-discharge deagglomeration action within the plume.

By way of more particular illustration, the example test results presented above in respect of the standard and high-flow inhalers might be utilised in example design methods to refine a design of an inhaler in accordance with the distinguishing features of the high-flow inhaler which were found to lead to advantageous alterations in the characteristics of the inhaler plume.

In particular, there may be provided in accordance with one or more aspects of the invention, a method of designing a dry powder inhaler wherein the dry powder inhaler is a breath-actuated dry powder inhaler comprising an airflow adaptor, the airflow adaptor comprising:

a first conduit having a proximal end and a distal end, wherein the proximal end allows fluid communication from a deagglomerator outlet port to the distal end of the first conduit, and at least one second conduit for allowing air to flow from a proximal end of the adaptor to a distal end of the adaptor independently of the airflow in the first conduit when a breath induced low pressure is applied to the distal end of the airflow adaptor, and wherein the method comprises testing the dry powder inhaler by means of a testing method described in any of the examples above; and if necessary, adjusting the design by adjusting a ratio of the sum of the cross-sectional areas of the at least one second conduit to the cross-sectional area of the first conduit to thereby alter one or more geometrical and/or dynamic characteristics of the dry powder plume discharged from the inhaler upon application of a breath induced low pressure to the distal end of the airflow adaptor.

The at least one second conduit changes the fluid dynamical properties of the consequently generated powder plume. In particular, it is to be expected that by increasing the proportion of air flowing through the at least one second conduit (i.e. the by-pass conduit), that the angle of deviation of the plume from horizontal may be decreased, and also the narrowness and concentration of the plume may be increased.

The extent of this adjustment depends upon the number of second conduits provided and also their cross-sectional areas. In particular, the magnitude of the adjustment to the plume characteristics may be varied by altering the ratio of the aggregate cross-sectional areas of the at least one second conduit to the cross-sectional area of the first conduit. By varying this design feature, the characteristic of the plume can be tuned.

In one embodiment the first dry powder inhaler 20 is a breath-actuated dry powder inhaler comprising an airflow adaptor 100, 200, 300, 50, 702, the airflow adaptor comprising:

a first conduit 101, 202, 302 having a proximal end and a distal end, wherein the proximal end allows fluid communication from a deagglomerator outlet port to the distal end of the first conduit, and at least one second conduit 304, 305, 306 for allowing air to flow from a proximal end of the adaptor to a distal end of the adaptor independently of the airflow in the first conduit 101, 202, 302 when a breath induced low pressure is applied to the distal end of the airflow adaptor, and wherein the method comprises adjusting a ratio of the sum of the cross-sectional areas of the at least one second conduit 304, 305, 306 to the cross-sectional area of the first conduit 101, 202, 302 so as to adjust vary one or more geometrical or dynamic characteristics of the dry powder plume discharged from the inhaler 20 upon application of a breath induced low pressure to the distal end of the airflow adaptor.

The present invention also provides a dry powder plume 24 generated by discharge from a dry powder inhaler 20, characterised in that:

an angle of deviation of a central axis 42 of an outer envelope shape of the discharged plume 24 with respect to an axis of orientation of a mouthpiece 22 of the inhaler is no greater than 8 degrees, and a cross-sectional area 44 of an outer envelope shape of the discharged plume 24 at a distance of 3 cm from a source of discharge of the plume is no greater than 5 cm$^2$.

Other variations to the disclosed embodiments can be understood and effected by those skilled in the art in practising the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention also consists in the subject-matter defined by the following numbered clauses:

1. A method of testing a dry powder inhaler comprising the steps of:

providing a dry powder inhaler (20) containing a dry powder formulation;

actuating the inhaler to discharge a dose of the dry powder formulation in the form of a dry powder plume (24);

illuminating the plume with a source of electromagnetic radiation (28);

capturing one or more images of a pattern of radiation reflected or diffracted by the electromagnetically illuminated plume (24); and processing the images to determine one or more geometrical and/or dynamical characteristics of the discharged plume (24).

2. A method as recited in clause 1, wherein the inhaler (20) is actuated within a vacuum chamber or an air flow chamber.

3. A method as recited in clause 1 or 2, wherein the source of electromagnetic radiation (28) comprises a source of visible light.

4. A method as recited in any preceding clause wherein the source of electromagnetic radiation (28) is a laser.

5. A method as recited in any preceding clause, wherein the method comprises capturing a plurality of images in series, and optionally wherein the images are captured at regular intervals at an interval frequency of from 300 to 1,000 Hz.

6. A method as recited in any preceding clause, wherein an outer envelope shape of the discharged plume (24) has a central axis (42) defining an angular orientation of the discharged plume, and wherein the method comprises analysing said angular orientation of the plume.

7. A method as recited in clause 6, wherein the dry powder inhaler (20) comprises a mouthpiece (22), and wherein the method comprises determining an angle of deviation of said central axis (42) of an outer envelope of the discharged plume (24) with respect to an axis of orientation of the mouthpiece.

8. A method as recited in any preceding clause, wherein the method comprises analysing a cross-sectional area (44) of an outer envelope shape of the discharged plume (24) at a given distance from a source of discharge of the plume, and optionally wherein said source of the discharge is defined as a distal end of a mouthpiece (22) of the inhaler (20).

9. A method as recited in any preceding clause, wherein the method comprises determining a powder concentration distribution across a given cross-section (44) of the discharged plume (24) at a given distance from a source of discharge of the plume.

10. A method of designing a dry powder inhaler (20), the inhaler being operable to discharge a dose of medicament in the form of a dry powder plume, the method comprising:

providing a first dry powder inhaler in accordance with a first design, the design intended to achieve a particular desired set of plume geometric and/or dynamic characteristics;

testing the dry powder inhaler (20) by means of a testing method defined in any preceding clause; and if necessary, adjusting the design of the first dry powder inhaler (20) based on results of said testing so as to better achieve the desired set of plume geometric and/or dynamic characteristics.

11. A method as recited in clause 10, wherein method comprises adjusting the design so as to minimise an angle of deviation of a central axis (42) of an outer envelope shape of the discharged plume (24) with respect to an axis of orientation of a mouthpiece (22) of the inhaler, and optionally wherein the mouthpiece defines a source of discharge of the plume.

12. A method as recited in clause 10 or 11, wherein the method comprises adjusting the design so as to reduce a cross-sectional area (44) of an outer envelope shape of the discharged plume (24) at a given distance from a source of discharge of the plume.

13. A method as recited in any of clauses 10 to 12, wherein the method comprises adjusting the design so as to alter a concentration distribution of the powder across a given cross-section (44) of the plume (24), the cross-section being located at a given distance from a source of discharge of the plume, and optionally wherein the design is adjusted so as to increase a concentration of the powder within a central region of the cross section, proximal to a central point of the cross section.

14. A method as recited in any of clauses 10 to 13, wherein the first dry powder inhaler (20) is a breath-actuated dry powder inhaler comprising an airflow adaptor (100, 200, 300, 50, 702), the airflow adaptor comprising:

a first conduit (101, 202, 302) having a proximal end and a distal end, wherein the proximal end allows fluid communication from a deagglomerator outlet port to the distal end of the first conduit, and at least one second conduit (304, 305, 306) for allowing air to flow from a proximal end of the adaptor to a distal end of the adaptor independently of the airflow in the first conduit (101, 202, 302) when a breath induced low pressure is applied to the distal end of the airflow adaptor, and wherein the method comprises adjusting a ratio of the sum of the cross-sectional areas of the at least one second conduit (304, 305, 306) to the cross-sectional area of the first conduit (101, 202, 302) so as to adjust vary one or more geometrical or dynamic characteristics of the dry powder plume discharged from the inhaler (20) upon application of a breath induced low pressure to the distal end of the airflow adaptor.

15. A dry powder plume (24) generated by discharge from a dry powder inhaler (20), characterised in that:

an angle of deviation of a central axis (42) of an outer envelope shape of the discharged plume (24) with respect to an axis of orientation of a mouthpiece (22) of the inhaler is no greater than 8 degrees, and a cross-sectional area (44) of an outer envelope shape of the discharged plume (24) at a distance of 3 cm from a source of discharge of the plume is no greater than 5 cm$^2$.

We claim:

1. A method of manufacturing a dry powder inhaler, the inhaler being operable to discharge a dose of medicament in a form of a dry powder plume, the method comprising:

providing a first dry powder inhaler in accordance with a first design, the first dry powder inhaler containing a dry powder formulation, and the first design intended to achieve a desired set of plume geometric and/or dynamic characteristics;

testing the first dry powder inhaler via a testing method comprising:

actuating the first dry powder inhaler to discharge a dose of the dry powder formulation in the form of a discharged dry powder plume, illuminating the plume with a source of electromagnetic radiation;

capturing one or more images of a pattern of radiation reflected or diffracted by an electromagnetically illuminated plume, and processing the images to determine a processed set of plume geometric and/or dynamic characteristics of the discharged dry powder plume, the processed set of plume geometric and/or dynamic characteristics being different than the desired set of plume geometric and/or dynamic characteristics; and based on the processed set of plume geometrical and/or dynamic characteristics of the discharged dry powder plume, modifying the first design of the first dry powder inhaler to generate a second design of a second dry powder inhaler having the desired set of plume geometric and/or dynamic characteristics.

2. The method of claim 1, wherein the inhaler is actuated within a vacuum chamber or an air flow chamber.

3. The method of claim 1, wherein the source of electromagnetic radiation comprises a source of visible light.

4. The method of claim 1, wherein the source of electromagnetic radiation is a laser.

5. The method of claim 1, wherein the testing method comprises capturing a plurality of images in series.

6. The method of claim 5, wherein the plurality of images are captured at regular intervals at an interval frequency of from 300 to 1,000 Hz.

7. The method of claim 1, wherein an outer envelope shape of the discharged dry powder plume has a central axis defining an angular orientation of the discharged dry powder plume, and wherein the testing method comprises analysing said angular orientation of the plume.

8. The method of claim 7, wherein the first dry powder inhaler comprises a mouthpiece, and wherein the testing method comprises determining an angle of deviation of said central axis of an outer envelope of the discharged dry powder plume with respect to an axis of orientation of the mouthpiece.

9. The method of claim 1, wherein the testing method comprises analysing a cross-sectional area of an outer envelope shape of the discharged dry powder plume at a given distance from a source of discharge of the plume.

10. The method of claim 9, wherein said source of the discharge is defined as a distal end of a mouthpiece of the first dry powder inhaler.

11. The method of claim 1, wherein the testing method comprises determining a powder concentration distribution across a given cross-section of the discharged dry powder plume at a given distance from a source of discharge of the plume.

12. The method of claim 1, wherein method comprises adjusting the design so as to minimise an angle of deviation of a central axis of an outer envelope shape of the discharged dry powder plume with respect to an axis of orientation of a mouthpiece of the inhaler.

13. The method of claim 12, wherein the mouthpiece defines a source of discharge of the plume.

14. The method of claim 1, wherein the method comprises adjusting the design so as to reduce a cross-sectional area of an outer envelope shape of the discharged dry powder plume at a given distance from a source of discharge of the plume.

15. The method of claim 1, wherein the method comprises adjusting the design so as to alter a concentration distribution of the powder across a given cross-section of the plume, the cross-section being located at a given distance from a source of discharge of the plume.

16. The method of claim 15, wherein the design is adjusted so as to increase a concentration of the powder within a central region of the cross section, proximal to a central point of the cross section.

17. The method of claim 1, wherein the first dry powder inhaler is a breath-actuated dry powder inhaler comprising an airflow adaptor, the airflow adaptor comprising:

a first conduit having a proximal end and a distal end, wherein the proximal end allows fluid communication from a deagglomerator outlet port to the distal end of the first conduit, and at least one second conduit for allowing air to flow from a proximal end of the adaptor to a distal end of the adaptor independently of the airflow in the first conduit when a breath induced low pressure is applied to the distal end of the airflow adaptor, and wherein modifying the first design includes modifying a ratio of a sum of cross-sectional areas of the at least one second conduit to a cross-sectional area of the first conduit to generate the second design of the second dry powder inhaler having the desired set of plume geometric and/or dynamic characteristics.

18. The method of claim 1 further comprising:

comparing the processed set of plume geometric and/or dynamic characteristics to the desired set of plume geometric and/or dynamic characteristics to generate a plume comparison.

19. The method of claim 1 further comprising:

fabricating the second dry powder inhaler according to the second design.

* * * * *